(12) United States Patent
Connell

(10) Patent No.: US 8,932,582 B2
(45) Date of Patent: Jan. 13, 2015

(54) CELL COMPOSITIONS AND USES THEREOF

(75) Inventor: David Connell, Hawthorn (AU)

(73) Assignee: Sportcell, Middlesex (GB)

( * ) Notice: Subject to any disclaimer, the term of this patent is extended or adjusted under 35 U.S.C. 154(b) by 555 days.

(21) Appl. No.: 13/128,176

(22) PCT Filed: Nov. 5, 2009

(86) PCT No.: PCT/GB2009/002615
§ 371 (c)(1),
(2), (4) Date: Aug. 31, 2011

(87) PCT Pub. No.: WO2010/052464
PCT Pub. Date: May 14, 2010

(65) Prior Publication Data
US 2011/0306946 A1 Dec. 15, 2011

(30) Foreign Application Priority Data
Nov. 7, 2008 (GB) .................................. 0820492.7

(51) Int. Cl.
*A61K 35/32* (2006.01)
*A61K 35/16* (2006.01)
*A61K 35/34* (2006.01)
*A61K 35/36* (2006.01)

(52) U.S. Cl.
CPC ................ *A61K 35/16* (2013.01); *A61K 35/32* (2013.01); *A61K 35/34* (2013.01); *A61K 35/36* (2013.01)
USPC ......................................... 424/93.7; 424/531

(58) Field of Classification Search
CPC ....... A61K 35/16; A61K 35/32; A61K 35/33; A61K 35/34; A61K 35/36; C12N 5/0656; C12N 5/0658
See application file for complete search history.

(56) References Cited

U.S. PATENT DOCUMENTS 6,673,603 B2 * 1/2004 Baetge et al. ................. 435/325

FOREIGN PATENT DOCUMENTS

| WO | WO 03/041568 | | 5/2003 | |
| WO | WO 2004/022078 | * | 3/2004 | ............. A61K 35/28 |
| WO | WO 2006/097701 | | 9/2006 | |

OTHER PUBLICATIONS

Vaculik et al, J Invest Dermatol, Mar. 2012, vol. 132, No. 3, pt. 1, pp. 563-574.*
Al-Nbaheen et al, Stem Cell Rev and Rep, 2013, vol. 9, pp. 32-43.*
Connell et al., "Treatment of lateral epicondylitis using skin-derived tenocyte-like cells," *British Journal of Sports Medicine*, BMJ Group, 43(4):293-298, 2009.
International Search Report, issued in International Patent Application No. PCT/GB2009/002615, mailed on May 19, 2010.
Sampson et al., "Platelet rich plasma injection grafts for musculoskeletal injuries: a review," *Current Reviews in Musculoskeletal Medicine*, 1(3-4):165-174, 2008.
Suresh et al., "Medial epicondylitis: is ultrasound guided autologous blood injection an effective treatment?" *British Journal of Sports Medicine*, 40(11):935-939, 2006.

* cited by examiner

*Primary Examiner* — Allison Fox
(74) *Attorney, Agent, or Firm* — Parker Highlander PLLC

(57) ABSTRACT

The present invention relates to blood serum and dermally-derived cells for use in tissue repair. Particularly it relates to blood serum and collagen producing cells for use in the treatment of connective tissue injuries. Preferably the cells and the blood serum are autologous and the connective tissue to be repaired is a tendon or ligament. Also provided is a method of treating connective tissue injuries by the administration of blood serum and collagen producing cells directly to the site of injury. It also relates to the use of blood serum and muscle-like cells for use in the treatment of muscle injury, particularly skeletal muscle injury.

14 Claims, 3 Drawing Sheets

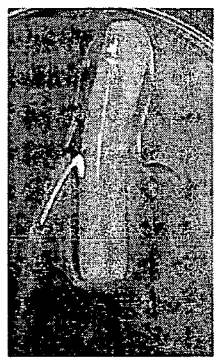
Fig 1
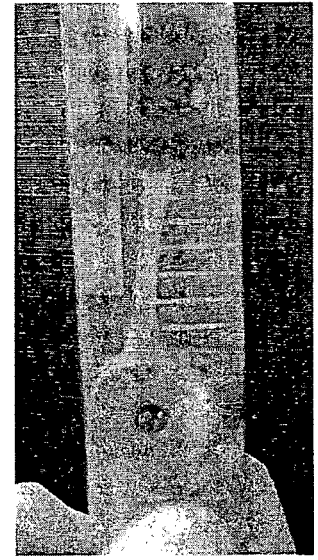
Fig 2
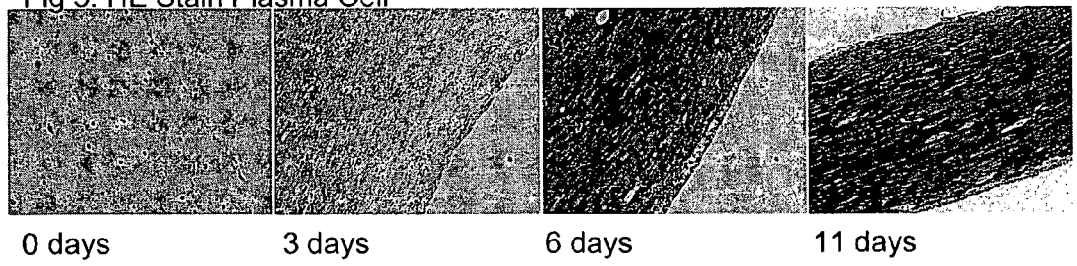
Fig 3. HE Stain Plasma Cell
0 days　　　3 days　　　6 days　　　11 days Fig 4:
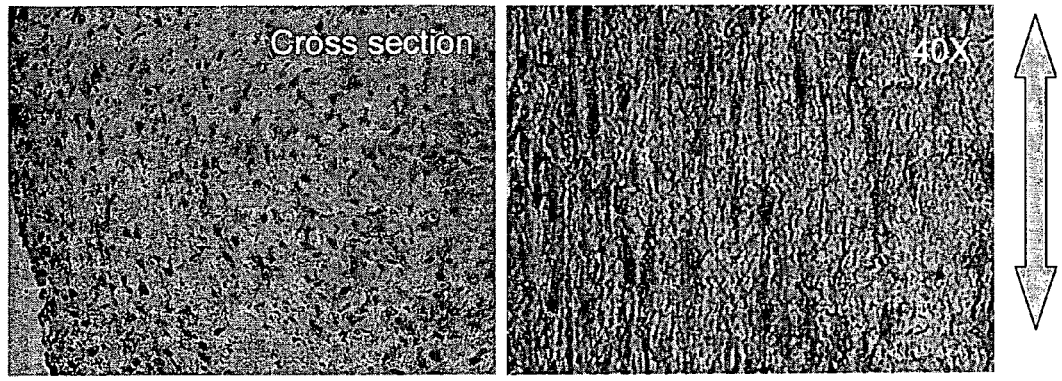
Fig. 4
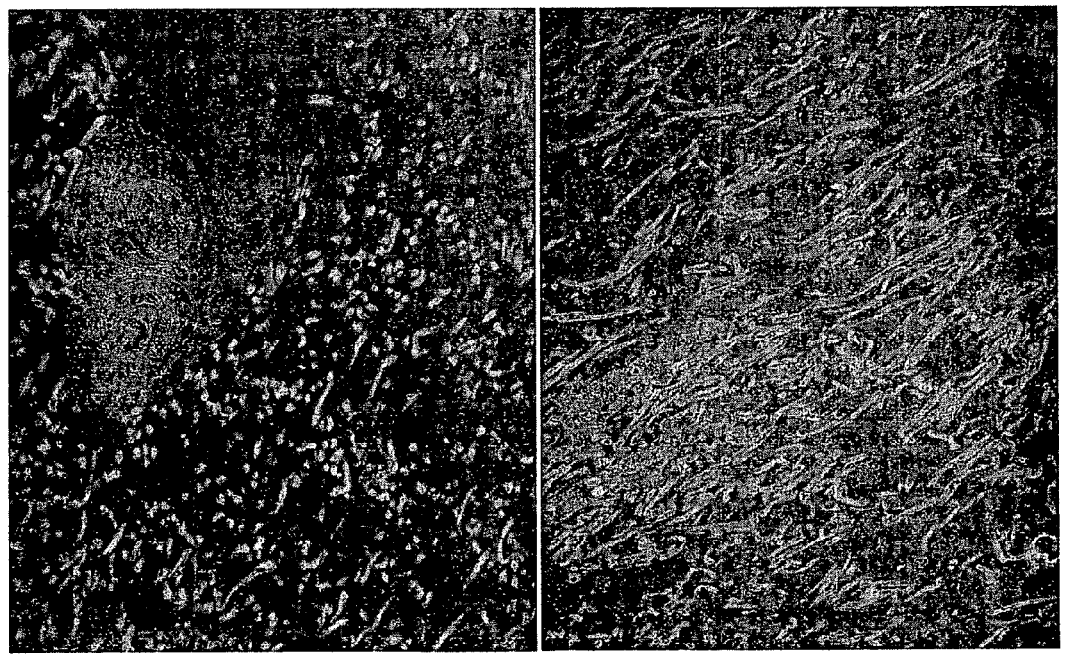
Fig. 5

CELL COMPOSITIONS AND USES THEREOF

CROSS-REFERENCE TO RELATED APPLICATIONS

This application is a national phase application under 35 U.S.C. §371 of International Patent Application No. PCT/GB2009/002615 filed Nov. 5, 2009 which claims priority to Great Britain Patent Application No. GB 0820492.7 filed Nov. 7, 2008. The entire text of each of the above-referenced disclosures are specifically incorporated herein by reference without disclaimer.

BACKGROUND OF THE INVENTION

1. Field of the Invention

The present invention relates to blood serum and dermally-derived cells for use in tissue repair. Particularly it relates to blood serum and collagen producing cells for use in the treatment of connective tissue injuries. Preferably the cells and the blood serum are autologous and the connective tissue to be repaired is a tendon or ligament. Also provided is a method of treating connective tissue injuries by the administration of blood serum and collagen producing cells directly to the site of injury. It also relates to the use of blood serum and muscle-like cells for use in the treatment of muscle injury, particularly skeletal muscle injury.

2. Description of Related Art

Injuries to connective tissue such as tendons or ligaments are known to take a very long time to heal, as long as several months or even years. In many cases, injuries to connective tissue such as the Achilles tendon or "tennis elbow" may never heal properly, necessitating surgical intervention. However, the tendon or ligament will never be the same as before injury since scar tissue will be present whether the injury is treated by non-surgical or surgical methods.

Normal tendons or ligaments are composed of arrays of collagen fibres (type I and type II) that are closely packed together. Collagen producing cells within the tendons, called tenocytes, produce the collagen molecules. Tendons are a mechanism by which muscles connect to bones which provide some elastic properties to modular forces, acting as springs in storing and releasing energy.

Ligaments attach bone to bone and also play a significant role in biomechanics. Both ligaments and tendons represent an orthopaedic challenge when damaged so it is very difficult, if not impossible, to restore the normal mechanical function of these tissues.

Treatment of tendon injury is rarely completely successful. Home treatment including rest, ice and over the counter pain relief such as ibuprofen may be sufficient. However, for more severe injuries, current treatments for tendonitis include strengthening exercises, soft tissue therapies, and physical therapy modalities. People with tendonitis and tendinosis may also benefit from a program of specific exercise designed to strengthen the force-absorbing capability of the muscle-tendon unit. Soft tissue therapies, like myofascial release, combined with new technology, such as the Theralase Cold Laser, has shown good success in treating these injuries.

Corticosteroid injections or topical applications may be used. Sometimes a doctor may inject a corticosteroid medication around a tendon to relieve tendonitis. Injections of cortisone reduce inflammation and can help ease pain temporarily. However, there are potential side effects. For example, repeated injections may weaken a tendon, increasing the risk of rupturing the tendon. Also, corticosteroid medications should never be directly injected into the tendon itself because this can contribute to tendon rupture. As an alternative to an injection, a corticosteroid solution can be topically applied to the painful region and drawn in through the skin using a gentle electric current via iontophoresis.

Another treatment method is dry needling. Dry needling is sometimes known as Western Acupuncture. The technique uses acupuncture needles inserted into specific trigger points that are commonly associated with acute and chronic musculoskeletal pain. Despite using acupuncture needles and some points that coincide with traditional Chinese acupuncture points, dry needling and Western acupuncture does not use any of the diagnostic or treatment philosophy associated with this system of healing. Dry needling is a discrete treatment system normally used as an adjunctive method of pain management of other therapies such as osteopathy. The therapeutic effect may be attributable to the induction of bleeding in the tendon.

The use of autologous blood injection is known to help with connective tissue injury. Direct injection of the patient's (autologous) blood into the tendon has been reported. Blood is drawn from the patient and centrifuged to increase the concentration of platelets. It is this fraction which is re-injected. The growth factors present in the blood promote healing in tendons, ligament and muscles. The injection site is identified and the needle guided by ultrasound imaging. Dry needling often accompanies the blood injection technique.

Disadvantages associated with these methods include scarring at the site of the tear or microtear, introduction of unwanted amounts of steroids into the system of the patient. Cell culture techniques have been used to generate tissue for repairing injured tissue in a patient. Cell culture techniques are various and widely described in the literature. In vitro studies utilise, in the main, monolayer culture techniques. Whilst these two-dimensional approaches offer a useful research tool, the lack of intact, in vivo characteristics and interactions limits their use. In order to generate tissue with structural integrity, numerous technologies have been developed which promote cell-cell and cell-matrix interaction to promote the creation of a three-dimensional structure for study or implant (WO03041568, WO04060426, WO06138552, WO08003320).

These techniques utilise mesenchymal stem cells (MSC)—often derived from bone marrow (U.S. Pat. No. 5,197,985), tenocytes and fibroblasts. MSC are favoured in cell therapy protocols because of their ability to differentiate into many other different types of cells including cartilage, bone, muscle, tendon, fibroblast and adipocyte (WO2004022078). Embryonic stem cells (ESC) are also used to create functional tissue grafts. As such, these techniques are primarily targeted at relatively large scale or acute tissue tears, to re-approximate two broken ends or for total tissue replacement.

Other types of cells have been used in cell therapy, including fibroblasts, osteoblasts and chondrocytes. To date, fibroblasts have been used as a component in a combinational closure for skin defects (WO02078721), as a cosmetic tool for aesthetics (DE69330129) and as a seed for synthetic and/or biodegradable matrices to generate three dimensional structures, pre-implantation and in vivo (U.S. Pat. No. 6,123,727, U.S. Pat. No. 6,140,039, U.S. Pat. No. 6,840,962, US2005060033, WO03043486, WO2001032129, CN1507926). Fibroblasts and fibroblast growth factor have been isolated from dermal tissue (WO03078607) and bone (WO05007811).

The implantation of cultured cells into a patient's tissue has the additional challenges of helping the implanted cells adapt to their new situation. Even when autologous cells from the patient's own body are used, the cells must still be integrated into the new site and use, or develop, means for receiving oxygen, sources of nutrition, and means for maintaining metabolic activity, amongst other adaptable functions. Cell culture techniques, treatable defects, factors that improve the successful adaptation of living cells to an implant site have also been described (WO08808229).

These embodiments of cell therapy include treating a defect in a patient with in vitro expanded cells and implanting into the tissue defect the cells with a helpful protein or other factor (e.g. proteins, macromolecules, molecules). Examples of such factors include immunogenic proteins, cell adhesion mediating proteins, apoptosis inhibitors (WO07035843), anoikis inhibitors (WO7035843), protease inhibitors, gene of interest, signal transduction proteins, anti-scarring agents (WO5051232), differentiation factors, vasodilators, angiogenesis proteins, pro-inflammatory proteins, pro-coagulation proteins, promoters of extracellular matrix (ECM) production (WO08070893), transport proteins, survival factors, a serum protein, cell culture serum-derived proteins and factors (WO9960951), chemoattractants (WO07022188), an ECM protein produced from culture (EP1263931), growth factor (WO03059932), cytokins (WO08086147), chemokines (WO05014026), hormones, space filling proteins and factors, soluble proteins, insoluble proteins, recombinant proteins, domains and fragments of proteins, peptides (WO0049136), gellable factors (WO0387303), amongst others that are apparent throughout the text and in the art. Depending on the application, other proteins and factors can be used that promote survival of the cells and optimize cell functionality.

More recently, and specific to the field of repair of chronic tendon tear in humans, studies utilizing autologous blood injection, proximal to and directly into the trauma site have demonstrated improved tissue repair characteristics. Treatments already known in this field includes the method of repairing tissue by the co-administration of blood components with a polymer which, on mixing turns into a non-liquid state to retain and adhere the therapeutic agents to the site of repair (US20020082220, US005709854, WO8064487) and the introduction of platelet-rich plasma (US6811777, WO08022651).

However there still remains a need for a reliable and effective method of tissue repair without the generation of scar tissue that provide reliable results in the healing of the tissue in a rapid efficient way with minimal disruption to the patient. There is a particular need for a treatment for connective tissue injury and muscle injury.

SUMMARY OF THE INVENTION

In this regard the present invention provides blood serum and dermally-derived cells for use in tissue repair. Particularly, the invention provides blood serum and collagen producing cells for use in the treatment of a connective tissue injury.

Alternatively, the invention provides blood serum and muscle-like cells for the treatment of muscle injury.

Preferably, the blood serum and the dermally-derived cells (the collagen producing cells or muscle-like cells) are autologous. Alternatively, allogeneic blood serum or cells may be used. By allogeneic it is meant blood serum (or whole blood), or cells from another patient of the same species. Alternatively, xenologous blood serum may be used, such as foetal bovine serum (FBS). FBS or other xenologous serum is only used if the donor's autologous blood is of poor optical quality.

The present invention is primarily useful for human patients, but may be useful for any other animal. In particular, horses, especially race horses, may benefit and also companion animals, such as dogs.

The blood serum may be part of whole blood, or may be obtained by removing the cellular components from whole blood, by centrifugation, or otherwise.

The connective tissue injury may be a tendon injury or pathology, such a trauma, a tear, a rupture. It may alternatively be a ligament injury.

The muscle injury may be a skeletal muscle tear, pull or strain.

Preferably, the collagen producing cells or muscle-like cells are derived from dermal tissue (but may be derived from other tissue types). The dermal tissue may be fibroblasts, which are cultured in such a way that they behave as tenocytes, or other collagen producing cells or cultured so that they behave as muscle cells. Most preferably the collagen produced by the cells is collagen type I or III, and not collagen type II, which is most usually associated with cartilage. The muscle cells are most preferably skeletal muscle cells.

In a preferred aspect of the invention, the blood serum and cells do not mix until immediately prior to contact with the injured tissue, i.e. they do mix immediately prior to contact with the injured tissue but not before administration. This may be achieved via a double chambered syringe, where final mixing of the cell suspension and blood serum takes place directly before injection. An example of such a syringe is shown in FIG. 7. Thus, the blood serum and cells are administrable by way of injection. The injection may be by way of an ultrasound-guided needle. This may apply to both collagen producing cells and blood serum for connective tissue injury and also to muscle-like cells and blood serum for muscle tissue injury.

In a most preferred aspect of the invention, the blood serum and collagen producing cells are at amounts of 250 µl to 5 ml of blood serum, and 5-100 million cells in approximately 250 µl to 5 ml medium, respectively. Preferably, the volume of cells is from 500 µl to 2 ml, most preferably, 500 µl. Preferably, the volume of blood serum or whole blood is from 500 µl to 2 ml, most preferably, 500 µl. Preferably the cells are at a concentration of 5-30 million cells, most preferably, the dose is about 10 million cells per total dose. However, numerous studies have shown that if the number of cells exceeds this, there are no harmful effects to the patient.

The blood serum and collagen producing cells are administered simultaneously to the site of the injury to repair the tendon or ligament with autologous tissue and blood factors avoiding the production of scar tissue and avoiding the administration of drugs such as steroids. The present invention also avoids the need for invasive surgery as the administration of the blood serum and cells is carried out through an ultrasound-guided needle.

The autologous cells are obtained by isolating cells, most preferably fibroblasts, from the dermal tissue, which are cultured to produce a cell culture containing at least five million cells in conditions to encourage the dermal cells to behave like tenocytes, i.e. the dermally-derived cells are cultured in a way such that they derive into collagen producing cells. The cultured cells are then injected into and around the site of connective tissue trauma with a co-administration of (preferably autologous) blood serum or whole blood. No synthetic or biodegradable matrixes are included, nor any synthetic polymers to form any matrix by cross-linking in vitro. No steroids or other drugs or medicines are required.

Preferably the collagen producing cells and the blood serum or whole blood are administered simultaneously to the site of connective tissue trauma. Most preferably this is done by the two compositions mixing immediately before contact with the site of injury, i.e. the compositions do not do mix outside of the injury site of the patient.

Once mixed, the cells and serum form a gel-like material which is able to fill up tears and gaps within the tendon or ligament structure. The collagen producing cells produce collagen which, upon normal use of the tendon or ligament (stretching), aligns in the correct orientation to successfully repair the tendon or ligament tear or other injury. No external or synthetic factors are required for this, i.e. no matrix, scaffold or the like is required for the collagen to fill the tear/gap and align correctly. Therefore no scar tissue or non-corrective tissue is present, meaning that the repaired corrective tissue is as it was before injury, and has as much strength and elasticity as the non-injured tissue. This provides a huge advantage over known methods, as described above.

The present inventive use may be repeated a further one, two or more times to accelerate healing of the injured tissue or to ensure complete repair of a particularly severe injury, such as a rupture. The repeated dose may increase or decrease the amount of blood serum or number of cells, or may be the same as the first dose.

The same preferred features apply when the injury is a muscle injury and the cells are muscle-like cells. It is the gentle use of the injured muscle that results in the correct alignment and regeneration of the muscle tissue by the muscle-like cells together with blood serum.

An example of a connective tissue disorder is tennis elbow, the common name for lateral epicondylitis. This is a well-known orthopaedic disorder of the common extensor tendon. It is related to over use and microtearing ending at the elbow where the muscle of the forearm joins the upper arm bone (humorous). Trauma may include microtears, bruising or inflammation. As mentioned above, home treatments such as rest, ice and anti-inflammatory medicine may help in repairing this trauma. However, reuse of the muscle or repetitive action that caused the trauma in the first place will severely hinder this repair process. Similar injuries and attempted repair by the body can be present in other connective tissue injuries such as the patellar ligaments (also called patellar tendons), Achilles tendon, the tendons and ligaments associated with the wrist, ankle, shoulder, etc. Other non-surgical methods can include corticosteroid injections and some injections may actually contribute to further injury of the connective tissue. They may help in the short term but have a high recurrence injury rate. Surgical methods carry the risks and expense of surgery as well as resulting scar tissue. By their nature, tendons and ligaments are elastic and spring-like whereas scar tissue is inelastic. Therefore, any tendon or ligament having scar tissue will have a reduced ability to stretch and spring back to its original length and use. This increases the likelihood of recurrent injury. Regarding the management of tendon or ligament injury there is a lack of consensus despite the advances in understanding of the cause of lateral epicondylitis and other tendon or ligament injuries. Numerous options have been advocated including rest, non-steroid or anti-inflammatory medication, bracing, physical therapy, iontophoresis, botulin toxin, extracorporeal shockwave therapy, buffered platelet rich plasma, dry needling and autologous blood injections. The resultant scar tissue formation utilizing these treatment options lacks the structural properties and mechanical strength of a normal tendon/ligament. None of these treatment strategies have attempted to regenerate connective tissue for reinforcement of the tensile strength.

Stem cells have been used to try and regenerate tissue. Stem cells are able to self renew, exist in an undifferentiated or unspecialised state and are capable of differentiation or specialisation along multiple lineages. Recent studies indicate that stem cells exist within different adult tissues including bone marrow, brain, dermis, periosteum, skeletal muscles, synovium, trabecular bone and vasculature. Previous studies in animal models have clearly proven that a regeneration of tendon tissue can be done by implantation of tendon or tendon like (tenocyte) cells with the ability to lay down a collagen matrix. Similarly, bone marrow derived mesenchymal stern cells have also been used for tendon tissue engineering. However many of these methods also use a synthetic or extracorporeal produced matrix upon which the stem cells can lie down and produce the new tendon tissue.

The dermally derived fibroblast cells produce collagen, which under normal physiological strain in a support matrix or tissue, align to affect a repair across a tissue lesion. This has been demonstrated using a skin biopsy which was cultivated in autologous serum as described below.

BRIEF DESCRIPTION OF THE DRAWINGS

FIG. 1 shows the plasma/cell construct produced in vitro as described in Example 2;

FIG. 2 shows the stretched plasma/cell construct;

FIG. 3 shows HE stained plasma/cell construct at different time points wherein at day 0 no staining is visible, and the staining accumulates over time indicating the integration of collagenous structures in the plasma/cell construct;

FIG. 4 shows the detail from FIG. 3 wherein in the left panel no orientation of fibres or cells can be seen in the cross section of the construct, and in the right panel the cells are orientated in the direction of the stretch and have elongated;

FIG. 5 shows an electron micrograph from non-stretched (left panel) and stretched (right panel) plasma/cell construct;

DETAILED DESCRIPTION OF THE ILLUSTRATIVE EMBODIMENTS

Figure 6:
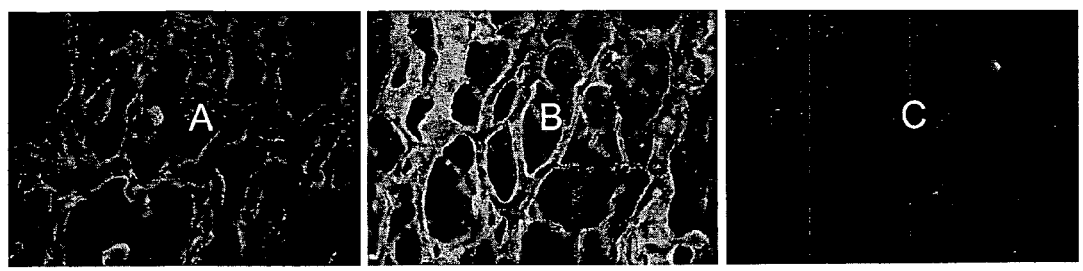
FIG. 6 shows collagen immunohistochemistry of frozen (TissueTek) specimens of the 11-day stretched construct which has been treated with an anti-collagen I antibody (left), an anti-collagen III antibody (middle) and anti-collagen II antibody (right) wherein it can be seen that positive staining was seen for collagen I and III and a negative staining for II.
Figure 7:
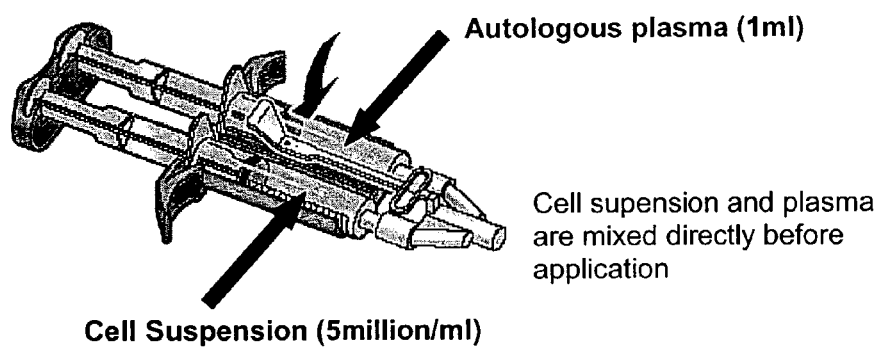
FIG. 7 showing a double chambered syringe suitable for administering the inventive compositions to a patient.

The present invention will now be described by way of the following non-limiting Examples.

EXAMPLES

Example 1

Treatment of "Tennis Elbow"

Obtainment of the Skin Biopsy

The skin biopsy and approximately 400 ml autologous blood are obtained in an operating theatre by a qualified and trained surgeon. The skin biopsy is packaged under aseptic conditions. During transport and up to the moment of processing, the sample is kept refrigerated)(4-10°.

Isolation and Cultivation of the Cells

The skin biopsy is washed in phosphate buffered saline (PBS) to remove debris and potentially contaminating organisms in the biopsy transportation medium. The skin biopsy is separated from obviously contaminating tissue like muscle etc, homogenised and transferred to sterile 50 ml tubes. The tissue is sedimented in a centrifuge. The muscle portion is stored for 24 to 72 hours at 2-8° C. The muscle tissue is sedimented by centrifugation. PBS is aspirated and the connective tissue portion is digested by adding a HEPES containing medium with collagenase and foetal calf serum.

14 to 24 hours later, PBS is added and the connective tissue is sedimented by centrifugation. The pellet is dispersed by adding fibroblast medium to each 50 ml tube. The medium with the muscle tissue pieces is transferred to tissue culture flasks, which are incubated for 48 to 72 hours in an incubator (5% $CO_2$, 37° C.). The proliferation medium is exchanged for fresh medium. Subsequently the medium is changed every 2 to 4 days. When the culture has reached approximately 80% confluence, the cells are detached from the culture flask via trypsinization, and seeded in a ratio of about 1:3 in a larger tissue culture flask. The step is repeated until the desired cell number is reached. To harvest the cells the flasks are washed with PBS and cells are trypsinized and resuspended in Cell Transportation Medium (CTM, Dulbecco Modified Eagle Medium/Ham's F12 (1:1, DMEM/F12) with 10% autologous serum). The cells are sedimented by centrifugation. The supernatant is aspirated and the cell pellet is resuspended and washed in CTM. The process is repeated. The resulting pellet is resuspended in CTM to give a final concentration of 10 million cells/ml.

Patient Recruitment

The clinical diagnosis of the tennis elbow was based on pain with point tenderness at the lateral epicondyle, with resistant wrist dorsiflexion, and with passive wrist flexion. Criteria for inclusion were symptomatic patients with clinical diagnosis of tennis elbow for at least 6 months, failure of conservative treatment including rest, physiotherapy and analgesics, and, confirmation of the diagnosis of MR imaging. The clinical diagnosis of internal impingement was further confirmed with MR imaging. The radiological interpretation was performed by a single consultant musculoskeletal radiologist (FA) experienced in sport-trauma MR imaging. All patients were imaged in the prone position with arms extended on a 1.5-Tesla scanner with a phased-array coil, matrix 256×192 and FOY 12 cm. The following MR pulse sequences were performed without using intra-articular gadolinium: spin-echo T1-weighted sagittal (TRJTE, 500-800/15-20); fast spin-echo T2-weighted in three planes (sagittal, coronal and axial) with fat saturation (3,000-5,000/50-65); and proton density in the coronal and axial planes (TRJTE, 4,000/13-20). The diagnosis of lateral epicondylitis was based on the presence of high-signal intensity focus on T2-weighted fat-suppressed MR images in the extensor carpi radialis brevis tendon at the lateral epicondyle. This finding was consistently present in all the symptomatic patients included in this study. Additional findings including marrow edema at the lateral epicondyle, joint effusion and increased signal intensity at the brachio-radialis tendon and radial collateral ligament were also identified.

Injection Technique Under Ultrasound-Guidance and Post-Procedure Protocol

Ultrasound was used to identify intra-substance tears and clefts within the injured tendon. Before cell-preparation injection, the site(s) of injury at the common extensor tendon were identified and documented. All the injections were performed under ultrasound guidance using the same positioning. At the start of the procedure, 2 ml of bupivacaine (0.25%) were infiltrated along the surface of the tendon using a 23 G needle. After a suitable interval of several minutes to allow the anaesthetic to work, the needle tip was positioned into the site of maximal tendon injury. Following this, the injectate of cell preparation was slowly introduced into the site of tendinosis and fibril discontinuity. This was done using a double-chambered delivery system containing equal amount (2 ml) of cell preparation injectate in one arm and centrifuged plasma concentrate in the other arm.

The total procedure time was kept to minimum ranging from 2-4 minutes. Approximately one-million fibroblast cells (approximately 2 ml, DMEM/F12 with 10% autologous serum) were injected at each intra-substance tear with an equal volume of autologous Sodium-Citrate Plasma.

Immediately after injection, the patient was kept in a supine position without moving the arm for 5 minutes. Patients were sent home with instructions to limit their use of the arm for next 24 hours and use paracetamol for pain, if necessary. The use of non-steroidal medication and any pain-provoking activities were prohibited. A follow-up appointment was scheduled at 6 weeks, 3 months and 6 months during which clinical and sonographic assessments were made.

Example 2

In Vitro Experiments to Determine Collagen Fibre Alignment

The intended and natural function of fibroblasts is to integrate into the ruptures of the tendon or ligament and to produce collagen to fill up the holes and ruptures within the tendon, or ligament.

In order to characterize the expanded cells towards this intended function, a huge effort following a tissue engineering approach was conducted.

The rationale was:

Can the cells survive in the plasma cell matrix?

Are the expanded cells able to sense the direction of the stretch present in every tendon or ligament and furthermore be able to react by building collagenous structures to be able to repair the ruptures in the tendon or ligament?

Which type of collagen is produced by the cells in the supposed tendon environment (stretch)?

Blood serum is blood plasma with some factors removed.

In order to achieve this, the connective tissue cells were mixed in an equal volume of autologous plasma and exposed to cyclic stretch for a prolonged period. The autologous plasma serves hereby as a matrix and biomaterial, which transduces stretch over the whole construct.

Methodology:

A skin biopsy of a 39 year old male was taken and cultivated in autologous serum as described above. After reaching the desired cell number, cells were harvested and approximately 7.5 million cells were resuspended in 1.5 ml medium with 10% autologous serum.

The cell suspension was mixed with autologous plasma/serum from the same individual and immediately filled into a 2.5 ml syringe. In the syringe, the plasma/cell suspension clotted and the resulting fibrin/cell construct was fixed in a stretching device. The construct was stretched about 20% of its length with an interval of 10 stretches/minute.

After the below indicated periods, the construct was fixed in paraformaldehyde and histologically examined (FIGS. 1 and 2).

Results:

The plasma cell construct was examined after 0, 3, 6 and 11 days in the stretching device. As can be seen in FIGS. 3 and 4, the amount of collagenous structures accumulate over time. Also the orientation of the fibrous bundles and cells in direction of the stretch can be seen in FIGS. 3 to 5.

CONCLUSION

The expanded cells produce collagen in high amounts after seeding into the plasma/fibrin-matrix. The unidirectional stretch as provoked in the stretching device-and present within the tendon or ligament upon normal movement leads to an orientation of cells in direction of the stretch and to a massive incorporation of collagenous structures within the construct. Isotyping of collagen revealed positive staining for Collagen I and III, which are typical for collagenous structures of the tendon or ligament. Staining for Collagen II, which is typical for cartilage tissue is negative. Results are shown in FIG. 6.

The above mentioned results have been confirmed by electron microscopy, which shows orientation of bundles in direction of the stretch, as shown in FIG. 5.

The invention claimed is:

1. A method for treating a connective tissue injury or connective tissue defect comprising administering to a subject (a) blood serum and (b) collagen producing cells derived from dermal tissue.

2. The method of claim 1, wherein the blood serum is autologous, allogeneic or xenologous to said subject.

3. The method of claim 1, wherein the collagen producing cells are autologous, allogeneic or xenologous to said subject.

4. The method of claim 1, wherein the blood serum is derived from blood plasma or whole blood.

5. The method of claim 1, wherein the connective tissue injury is a tendon injury or a ligament injury.

6. The method of claim 5, wherein said tendon injury or ligament injury is a tear, bruise or rupture.

7. The method of claim 1, wherein the blood serum and collagen producing cells are mixed immediately prior to contact with the injured tissue.

8. The method of claim 1, wherein the blood serum and collagen producing cells or muscle-like cells are administered by injection.

9. The method of claim 8, wherein the injection is by ultrasound-guided needle.

10. The method of claim 1, wherein the collagen producing cells are cultured prior to use.

11. The method of claim 1, wherein the concentration of collagen producing cells is from 5 to 100 million cells per ml.

12. The method of claim 1, wherein said blood serum and collagen producing cells are administered directly to the injury site.

13. The method of claim 12, wherein administration of cells and blood serum is simultaneous.

14. The method of claim 1, wherein the collagen producing cells are administered more than once.

* * * * *

UNITED STATES PATENT AND TRADEMARK OFFICE
CERTIFICATE OF CORRECTION

PATENT NO. : 8,932,582 B2
APPLICATION NO. : 13/128176
DATED : January 13, 2015
INVENTOR(S) : David Connell Page 1 of 1

It is certified that error appears in the above-identified patent and that said Letters Patent is hereby corrected as shown below:

In the Claims

In claim 8, column 10, line 13, delete the phrase "or muscle-like cells".

Signed and Sealed this
Twenty-first Day of April, 2015

Michelle K. Lee
*Director of the United States Patent and Trademark Office*